(12) United States Patent
Rimando

(10) Patent No.: US 8,697,090 B2
(45) Date of Patent: *Apr. 15, 2014

(54) METHOD OF TREATING PERSISTENT GENITAL AROUSAL DISORDER WITH A NEUROTOXIN

(75) Inventor: Marlon P. Rimando, Livingston, NJ (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/464,562

(22) Filed: May 4, 2012

(65) Prior Publication Data

US 2012/0282241 A1    Nov. 8, 2012

Related U.S. Application Data

(60) Provisional application No. 61/482,991, filed on May 5, 2011.

(51) Int. Cl.
*A61K 39/02* (2006.01)
*A61K 39/08* (2006.01)

(52) U.S. Cl.
USPC .................................. 424/236.1; 424/247.1

(58) Field of Classification Search
USPC ............................................ 424/247.1, 236.1
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 6,063,768 A | 5/2000 | First |
| 6,139,845 A | 10/2000 | Donovan |
| 6,299,893 B1 | 10/2001 | Schwartz et al. |
| 6,306,423 B1 | 10/2001 | Donovan et al. |
| 6,312,708 B1 | 11/2001 | Donovan |
| 6,423,319 B1 | 7/2002 | Brooks et al. |
| 6,447,787 B1 | 9/2002 | Gassner |
| 6,458,365 B1 | 10/2002 | Aoki et al. |
| 6,464,986 B1 | 10/2002 | Aoki et al. |
| 7,238,357 B2 | 7/2007 | Barron |
| 7,658,933 B2 | 2/2010 | Foster et al. |
| 7,659,092 B2 | 2/2010 | Foster et al. |
| 2003/0224019 A1 | 12/2003 | O'Brien |
| 2004/0009180 A1 | 1/2004 | Donovan |
| 2007/0269463 A1 | 11/2007 | Donovan |
| 2010/0034802 A1 | 2/2010 | Foster et al. |
| 2012/0251518 A1* | 10/2012 | Blumenfeld et al. ...... 424/94.63 |

FOREIGN PATENT DOCUMENTS

WO    WO03-011333    2/2003

OTHER PUBLICATIONS

Waldinger et al. New Insights Into Restless Genital Syndrome: Static Mechanical Hyperesthesia and Neuropathy of the Nervus Dorsalis Clitoridis; The Journal of Sexual Medicine, vol. 6, No. 10 (2009) pp. 2778-2787.*

* cited by examiner

*Primary Examiner* — Susan Hanley
*Assistant Examiner* — Paul Martin
(74) *Attorney, Agent, or Firm* — Brigitte C. Phan; Ted Chan; Debra Condino

(57) ABSTRACT

A method of controlling dysregulation of the dorsal cutaneous nerve of the clitoris and, in particular, a method for treating PGAD is provided. In one aspect, the method comprises administering a neurotoxin, such as a botulinum toxin, to the clitoral area of the human in need of treatment.

18 Claims, No Drawings

METHOD OF TREATING PERSISTENT
GENITAL AROUSAL DISORDER WITH A
NEUROTOXIN

CROSS REFERENCE

This application claims the benefit of priority pursuant to 35 U.S.C. §119(e) to U.S. provisional patent application Ser. No. 61/482,991, filed May 5, 2011, incorporated entirely by reference.

BACKGROUND OF THE INVENTION

Persistent Genital Arousal Disorder (PGAD) results in a spontaneous, persistent, and uncontrollable genital arousal, with or without orgasm or genital engorgement, unrelated to any feelings of sexual desire. It is a disabling condition caused by dysregulation of the dorsal sensory nerve, a distal branch of the pudendal nerve located bilateral to the vagina and clitoris. This condition has also been called Restless Genital Syndrome (RGS) and Persistent Sexual Arousal Syndrome (PSAS).

Physical arousal caused by this disorder can be very intense and persist for extended periods. Orgasm can provide temporary relief, but within hours the symptoms can return. Failure or refusal to relieve the symptoms often results in waves of spontaneous orgasms in women and ejaculation in men. The symptoms can be debilitating, preventing concentration on mundane tasks. Certain situations, such as riding in an automobile or train, or vibrations from mobile phones, can aggravate the condition, causing the discomfort to verge on pain. It is not uncommon for sufferers to lose some or all sense of pleasure over the course of time as release becomes associated with relief from pain rather than the experience of pleasure.

The cause or causes of PGAD are not yet known, though relief of symptoms has been noted from treatment with varenicline, as well as the use of antidepressants, antiandrogenic agents and anesthetizing gels. Psychotherapy with cognitive reframing of the arousal as a healthy response has also been used.

The genus *Clostridium* includes over one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. Seven generally immunologically distinct botulinum neurotoxins have been characterized, these being respectively botulinum neurotoxin serotypes A, B, $C_1$, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B.

A commercially available botulinum toxin-containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract.

A botulinum toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), nerve entrapment syndromes (U.S. Published Patent Application 20030224019, filed Feb. 27, 2003), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. Published Patent Application No. 20040009180, filed Jul. 11, 2002), all herein incorporated entirely by reference.

An approach currently being exploited to expand Clostridial toxin-based therapies involves modifying a Clostridial toxin such that the modified toxin has an altered cell targeting capability for a neuronal or non-neuronal cell of interest. Called re-targeted endopeptidases or Targeted Vesicular Exocytosis Modulator Proteins (TVEMPs), these molecules achieve their exocytosis inhibitory effects by targeting a receptor present on the neuronal or non-neuronal target cell of interest. This re-targeted capability is achieved by replacing the naturally-occurring binding domain of a Clostridial toxin with a targeting domain (or targeting moiety) showing a selective binding activity for a non-Clostridial toxin receptor present in a cell of interest. Such modifications to the binding domain result in a molecule that is able to selectively bind to a non-Clostridial toxin receptor present on the target cell. A re-targeted endopeptidase can bind to a target receptor, translocate into the cytoplasm, and exert its proteolytic effect on the SNARE complex of the neuronal or non-neuronal target cell of interest.

An important difference between re-targeted endopeptidases such as TVEMPs and native Clostridial toxins is that because the TVEMPs do not target motor neurons, the lethality associated with over-dosing a mammal with a TVEMP is greatly minimized, if not avoided altogether. For example, opioid TVEMPs can be administered at 10,000 times the therapeutically effective dose before evidence of lethality is observed, and this lethality is due to the passive diffusion of the molecule and not via the intoxication process. Thus, for all practical purposes TVEMPs are non-lethal molecules. Additional disclosure relating to TVEMPs can be found in U.S. application Ser. No.'s 12/303,078 and 12/868,510, both incorporated entirely by reference.

DETAILED DESCRIPTION

PGAD caused by dysregulation of the dorsal cutaneous nerve of the clitoris results from inappropriate release of neuromodulators. Neurotoxins, such as, for example, Clostridial neurotoxins, can be used to inhibit this release. This inhibition modulates the dysregulation of the dorsal cutaneous nerve.

In one embodiment, the neurotoxin is a botulinum toxin, such as a botulinum toxin type A, for example.

As used herein, the following definitions are provided.

About: as used herein "about" means approximately or nearly and in the context of a numerical value or range set forth means ±15% of the numerical value range recited or claimed.

Enhancing agent: as used herein "enhancing agent" refers to an agent that enhances the permeability so that botulinum toxin can be absorbed, for example when administered to a gastrointestinal tract, to achieve the therapeutic effect. In reference to the disclosure herein, enhancing agent can include dimethylsulfoxide (DMSO), hyaluronidase or a combination of pluronic lecithin organizer (PLO) and DMSO. An enhancing agent may include, and are not limited to, liposomes; transfersomes; lecithin vesicles; ethosomes; water; surfactants, such as anionic, cationic, and nonionic surfactants; polyols; and essential oils.

Local administration: as used herein "local administration" or "locally administering" means direct administration of a pharmaceutical at, or to the vicinity of, a site on or within an animal body, at which site a biological effect of the pharmaceutical is desired. One example of local administration can include direct injection of a botulinum toxin. Topical administration as utilized herein is a type of local administration in which a pharmaceutical agent is applied to a person's periclitoral area, such as for example to the periclitoral area to which botulinum toxin, for example, is to be administered in accordance with the teachings presented herein.

Neurotoxin: as used herein "neurotoxin" means a biologically active molecule with a specific affinity for a cell surface receptor of motor neurons (also known as efferent or effector neurons). Neurotoxin includes Clostridial toxins, such as Clostridial botulinum toxins, both as non-complexed toxin (having a molecular weight of about 150 kDa) and as complexed with one or more non-toxin, toxin associated proteins; the complexes having molecular weights of about 900 kD, 700, kD, 500 kD or 300 kD, for example. Botulinum toxins can include toxins that are recombinantly made and modified in accordance with known molecular techniques, that is, a modified neurotoxin means a neurotoxin which has had one or more of its amino acids deleted, modified or replaced (as compared to the native neurotoxin) and includes neurotoxins made by recombinant technology as well as variants and fragments of a native or recombinantly produced neurotoxin.

Endopeptidase: as used herein, "endopeptidase" means a biologically active molecule with a specific affinity for a cell surface receptor of sensory neurons (also known as afferent or receptor neurons). Sensory neurons carry nerve impulses from receptors or sense organs towards the central nervous system. Endopeptidases such as TVEMPs decrease the effects of sensory afferents, including conditions that are predominantly motor in origin. See, for example, U.S. Pat. No. 7,658,933 to Foster et al., titled "Non-Cytotoxic Protein Conjugates"; U.S. Pat. No. 7,659,092 to Foster et al., titled "Fusion Proteins"; and U.S. Ser. No. 12/303,078 to Foster et al., titled "Treatment of Pain," all incorporated entirely by reference. In addition, endopeptidases can modulate pain associated with multiple medical conditions.

Treating: as used herein "treating" or "to treat" means to alleviate, modulate, or eliminate either a symptom of a condition or disorder or the condition or disorder itself.

Targeting Moiety: as used herein "targeting moiety" means any chemical structure associated with an agent that functionally interacts with a binding site to cause a physical association between the agent and the surface of a target cell.

Therapeutically effective: as used herein "therapeutically effective" means an amount of toxin administered that will reduce or ameliorate a condition or symptom (in frequency and/or intensity) in a subject. The therapeutically effective amount of toxin, such as a botulinum neurotoxin, delivered to a subject, is an amount that achieves a desired effect yet does not result in undesirable systemic side effects associated with systemic neurotoxin poisoning, as known by those of ordinary skill in the art.

In one embodiment of the invention, a method of treating PGAD in a human is disclosed, comprising the step of administering a composition comprising a neurotoxin to a human in need thereof. In certain embodiments, the human is a woman, of any age, race, or ethnicity. In some embodiments, the human is a pre-, peri-, or post-menopausal woman. In one example, the composition is administered to the periclitoral area or a portion thereof. In a particular embodiment, the composition is administered to the clitoris. In yet another embodiment, the human is a woman with PGAD or at risk for developing PGAD. When the woman is at risk of developing PGAD, the composition can be administered prophylactically to slow the onset or prevent the onset of PGAD. In another embodiment, the composition can be administered to a woman at risk of developing PGAD due to hormonal disorders, medication, or genetic conditions that are associated with the development of PGAD.

In one embodiment, a method of modulating PGAD is provided, comprising administering a composition comprising a neurotoxin to a human in need thereof. In certain embodiments, the human is a woman, of any age, race, or ethnicity. In some embodiments, the human is a pre-, peri-, or post-menopausal woman. In yet another embodiment, the human is a woman with PGAD or at risk for developing PGAD. When the woman is at risk of developing PGAD, the composition can be administered prophylactically to slow the onset or prevent the onset of PGAD. In another embodiment, the composition can be administered to a woman at risk of developing PGAD due to hormonal disorders, medication, or genetic conditions that are associated with the development of PGAD.

In another embodiment, a method is provided for treating a symptom of PGAD, comprising administering a composition comprising a neurotoxin to a human in need thereof.

Methods of composition administration useful for the practice of particular embodiments disclosed herein include, but are not limited to, instillation, oral administration, topical administration (that is, to the clitoris region or portions thereof), direct injection, implantation of a neurotoxin-containing implant, or any combination thereof. In the case of administration via direct injection, such injections can be performed percutaneously. In certain embodiments the composition can comprise an enhancing agent.

In certain embodiments, the neurotoxin utilized is a botulinum toxin, wherein the botulinum toxin is selected from the group consisting of botulinum toxin type A, B, C, D, E, F, and G. In a most preferred embodiment, the neurotoxin utilized in accordance with the teaching presented herein is a botulinum toxin type A. In particular embodiments the quantity of neurotoxin administered is from about 1 unit to about 10,000 units. As an example, where the neurotoxin is a botulinum toxin type A, the amount administered is from about 1 unit to about 150 units of the botulinum toxin. In one regimen, neurotoxin is administered about every 1 to about every 12 months to the patient in need thereof.

In certain embodiments, the composition comprises an endopeptidase such as, for example, a TVEMP. In certain embodiments, the neurotoxin can be a neurotoxin comprising an un-modified targeting moiety, because in certain embodiments both TVEMPS and neurotoxins comprising an un-modified targeting moiety can effectively treat similar conditions or disorders, though the molecules target different cells. In certain embodiments, the composition comprises both a TVEMP and a neurotoxin comprising an un-modified targeting moiety.

In another aspect, a method of inhibiting PGAD in a human is provided herein, comprising the step of administering a composition containing a neurotoxin to the gastrointestinal tract of the human. As above, the neurotoxin can be a botulinum toxin selected from the group consisting of botulinum toxin types A, B, C, D, E, F, and G, more preferably botulinum toxin type A or type B. In certain embodiments the neurotoxin can be a TVEMP.

In certain embodiments the neurotoxin is a botulinum toxin selected from the group consisting of type A, B, C, D, E, F, G, and a combination thereof. Exemplary, commercially available, botulinum toxin containing compositions include, but are not limited to, BOTOX®, DYSPORT® (*Clostridium botulinum* type A toxin hemagglutinin complex with human serum albumin and lactose in the formulation), available from Ipsen Limited, Berkshire, U.K. as a powder to be reconstituted with 0.9% sodium chloride before use) and MYOBLOC® (an injectable solution comprising botulinum toxin type B, human serum albumin, sodium succinate, and sodium chloride at about pH 5.6, available from Solstice Neurosciences, Inc., South San Francisco, Calif.). XEOMIN® (a 150 kDa botulinum toxin type A formulation is also available from Merz Pharmaceuticals, Potsdam, Germany) is another useful neurotoxin which can be used as set forth and in accordance with the teachings herein disclosed.

The amount of toxin or endopeptidase administered according to a method within the scope of the present disclosure can vary according to the particular condition being treated, including its severity and other various patient variables including size, weight, age, and responsiveness of the particular patient to the botulinum neurotoxin therapy. To guide the practitioner, typically, no less than about 5 units and no more than about 100 units of a botulinum toxin type A (such as BOTOX®) is administered per injection site (e.g. to the clitoris area), per patient treatment session. For topical applications, more toxin can be used, as application to the epidermis, or selected portions thereof, as herein described herein, as absorption is relied upon for uptake rather than direct injection. For a botulinum toxin type A such as DYSPORT®, preferably no less than about 15 units and no more about 300 units of the botulinum toxin type A are administered per administration or injection site, per patient treatment session. For a botulinum toxin type B such as MYOBLOC®, preferably no less than about 150 units and not more than 50,000 units and preferably not more about 10000 units of the botulinum toxin type B are administered per administration or injection site, per patient treatment session. Less than about 5, 15 or 150 units (of BOTOX®, DYSPORT® and MYOBLOC® respectively) may fail to achieve a desired therapeutic effect, while more than about 100, 300 or 10,000 units (of BOTOX®, DYSPORT® and MYOBLOC® respectively) may result in clinically observable side effects which can vary depending on administration method, site and particular patient.

For example and in particular embodiments, an implant that slowly releases a therapeutically effective amount of botulinum toxin or endopeptidase can obviously contain an amount of toxin (i.e. of units) that may be higher than an amount that is typically administered, directly (e.g., by subdermal injection). As an illustrative example, while 1000 units of BOTOX® may not be desired to be administered at one time to a target via a syringe, yet these same 1000 units, when incorporated into a slow-release implant that is placed adjacent a clitoral portion of the patient in need of botulinum toxin administration in accordance with the present disclosure, can provide slow, long term dosing/release of botulinum neurotoxin in therapeutically effective amounts. An example of a range of units of botulinum toxins delivered orally, via injection, and via implant, according to one embodiment of the invention, is shown in Table 1.

TABLE 1

|  | ORAL | INJECTION | IMPLANT |
|---|---|---|---|
| BOTOX ® | 100-500 | 50-250 | 25-500 |
| DYSPORT ® | 300-1500 | 150-750 | 75-1000 |
| XEOMIN ® | 100-500 | 50-250 | 25-500 |
| MYOBLOC ® | 10,000-50,000 | 5,000-25,000 | 2500-25,000 |

Formulation of botulinum toxin for ingestion is known in the art (see for example, U.S. Pat. No. 7,238,357, herein incorporated by reference) and formulation of orally ingested pharmaceuticals that release actives in such a formulation at particular gastrointestinal regions in known in the art.

In additional embodiments, no less than about 10 units and no more about 400 units of BOTOX®; no less than about 30 units and no more than about 1600 units of DYSPORT®; and no less than about 250 units and no more than about 20000 units of MYOBLOC® are administered per site, per patient treatment session.

In still further embodiments, no less than about 20 units and no more about 300 units of BOTOX®; no less than about 60 units and no more than about 1200 units of DYSPORT®, and; no less than about 1000 units and no more than about 15000 units of MYOBLOC® are administered per site, per patient treatment session. There can be multiple injection sites (i.e. a pattern of injections) for each patient treatment session in order to distribute the neurotoxin over a desired target area, such as around/throughout the vulva, particularly the periclitoral area, more particularly, the clitoris.

Although examples of routes of administration and dosages are provided, the appropriate route of administration and dosage are generally determined on a case-by-case basis by the attending physician, as known in the botulinum toxin arts, and titration of the dosage to a therapeutically effective one, for a particular patient/condition, is routinely undertaken. Such determinations are routine to one of ordinary skill in the art (see for example, Harrison's Principles of Internal Medicine (1998), edited by Anthony Fauci et al., 14th edition, published by McGraw Hill). For example, the route and dosage for administration of a composition according to the present disclosed invention can be selected based upon criteria such as the solubility characteristics of the neurotoxin chosen as well as the intensity and scope of the condition to be treated.

Additionally, in some embodiments, a physician may have to alter dosage in each case (i.e. patient) in accordance with the assessment of the severity of the condition, as typically done when treating patients with a condition/disorder. Further, in some embodiments, the treatment may have to be repeated at least one additional time, in some cases several times, depending on the severity of the condition and the patient's overall health. If, for example, a patient is not deemed physically suitable for a full administration of botulinum toxin or endopeptidase, or if a full administration is not desired for any reason, smaller doses on multiple occasions may prove to be efficacious. Further still, if botulinum toxin or endopeptidase is administered at a certain dosage that is not sufficient to attain the desired treatment goal, such as reduction in PGAD symptoms over a particular time period, the dose may be increased for a second and subsequent administration session(s) by the attending physical as he/she best sees fit (i.e. a dose finding regimen).

Although one exemplary composition may only contain a single type of neurotoxin, such as botulinum toxin type A, as the active ingredient to treat PGAD, other therapeutic compositions may include two or more types of neurotoxins, which may provide enhanced therapeutic effects of the disorders. For example, a composition administered to a patient may include botulinum toxin type A and botulinum toxin type B. Administering a single composition containing two different neurotoxins can permit the effective concentration of each of the neurotoxins to be lower than if a single neurotoxin is administered to the patient while still achieving the desired therapeutic effects.

In certain embodiments, it is desirable for the neurotoxin to be administered to the vulva. In other embodiments, the neurotoxin is administered to the periclitoral area and in yet other embodiments, the neurotoxin is administered to the clitoris. In one embodiment, the neurotoxin can be administered to the epidermal surface of the clitoris. In yet another embodiment, the neurotoxin is administered to the dermis of the clitoris. In this embodiment, care is taken to avoid the urethra, found toward the inferior portion of the clitoris and the anatomic structure from which urine is released. In one embodiment, about 10 to about 100 units of neurotoxin are distributed, via, for example, by injection, at about 10 to about 20 sites along the epidermal area surrounding the clitoris.

The neurotoxin can be administered to the clitoris using one or more routes, including but not limited to, orally, topically, transdermally, intravenously, by implant, by instillation or percutaneously (by injection). Visual guidance may be required and can be provided by radiograph, fluoroscopy, CT, MRI, ultrasound, and a combination thereof. These techniques of administration and guidance are well known to those of skill in the art.

In certain embodiments the composition is administered orally. The therapeutic dose of orally administered neurotoxin is such that there are nominal or insignificant systemic effects due to any neurotoxin that is absorbed through the gut lining in to the circulatory system (for details, see U.S. Published Patent Application No. 2007/0269463, incorporated herein by reference in its entirety). An orally administered neurotoxin can remain bioactive in the harsh environment of the gastrointestinal tract, and is prepared so that the neurotoxin is substantially uniformly dispersed in a biodegradable carrier. An alternate oral formulation can comprise a carrier coated by a biodegradable coating, and either the thickness of the coating or the coating material can be varied. Further, the neurotoxin can be in a controlled-release composition. The thickness of the oral formulation can be used to control the absorption of water by, and thus the rate of release, of a neurotoxin from the formulation. Thicker oral formulations release botulinum toxin more slowly than thinner ones. The oral formulations include excipients, such as bulking agents, stabilizing agents, buffers, etc. The oral formulation can be in any suitable oral form, including but not limited to a capsule, tablet, gelcap, and a liquid.

In embodiments where the neurotoxin is administered by implant, release of the neurotoxin is achieved over a period of time, from hours, to days, to weeks. For example, the neurotoxin can be released from about 1 hour to about 4, or 8, or 12 weeks. Monophasic or pulsatile release of the neurotoxin can be achieved utilizing one or more implants. In certain embodiments, a plurality of implants can be used with the same or differing carrier material compositions. Further, the neurotoxin can be encapsulated in one or more types of microspheres having the same or differing degradation patterns such that the neurotoxin can be released at similar or differing rates, respectively. In one embodiment, one or more implants are implanted subcutaneously to the clitoris. Additional detail regarding implants is provided in U.S. Pat. No. 6,506,399, incorporated herein by reference in its entirety.

The botulinum toxins described herein can be incorporated into a topical formulation, as known in the art. Preferably, the compositions can more easily allow the application of the botulinum toxin into the target site in a patient. Suitable compositions include, but are not limited to creams, lotions, hydrogels, jellies, sprays, pastes, adhesives, emulsions, nanoparticles, microparticles, drops, powders, and combinations thereof. Methods for administering a botulinum toxin to the clitoris are well known in the art, (e.g. U.S. Pat. No. 5,437,291, herein incorporated by reference in its entirety), and such apparatus can be utilized in order to practice particular embodiments in accordance with the teachings provided herein.

In certain embodiments, treatments are limited to female patients.

The botulinum toxins used herein inhibit neuromodulator production. The suppressive effects provided by the toxin can persists for several months, such as from about 1 month to about 12 months, or from about 1 month to about 6 months. In one embodiment, the suppression can last for years, for example up to about 2 years, for example, if the botulinum toxin is supplied in a slow release implant form.

EXAMPLE 1

Treatment of PGAD with Botulinum Toxin A

A 44 year old woman presents with PGAD. Patient is administered 5 units of botulinum toxin A, subcutaneously, at 15 sites distributed along the periclitoral surface of the vulva. After a period of 3 months, the patient shows decreased symptoms, indicative of decreased dysregulation.

EXAMPLE 2

Treatment of PGAD with Botulinum Toxin B

A 61 year old woman presents with an idiopathic increase in arousal. Patient is topically administered 25,000 units of botulinum toxin B every 6 months for a period of 1.5 years. Patient is evaluated 2 years from the date of the first treatment and shows decreased symptoms indicative of decreased dysregulation.

EXAMPLE 2

Treatment of PGAD with a TVEMP

A 41 year old woman presents with PGAD. Patient is topically administered 15,000 units of a TVEMP targeted toward the sensory nerves in the clitoris every 6 months for a period of 1 year. Patient is evaluated 2 years from the date of the first treatment and shows decreased symptoms indicative of dysregulation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A method of treating Persistent Genital Arousal Disorder (PGAD) in a human comprising: administering a composition comprising a neurotoxin to a human in need thereof, wherein the neurotoxin is a native botulinum toxin, thereby treating PGAD in the human.

2. The method of claim 1, wherein the neurotoxin is administered to the vulva.

3. The method of claim 2, wherein the neurotoxin is administered to the peri-clitoral area.

4. The method of claim 3, wherein the neurotoxin is administered to the clitoris.

5. The method of claim 2, wherein the neurotoxin is administered via instillation, orally, topically, via injection, via implant, or a combination thereof.

6. The method of claim 5, wherein the injection is administered percutaneously, cystoscopically, or a combination thereof.

7. The method of claim 1, wherein the botulinum toxin is selected from the group consisting of botulinum toxin type A, B, C, D, E, F, and G.

8. The method of claim 7, wherein the neurotoxin is botulinum toxin type A.

9. The method of claim 1, wherein the neurotoxin is a botulinum toxin type A and is administered in an amount of from about 1 unit to about 2750 units.

10. The method of claim 9, wherein the neurotoxin is administered about every 1 to about 12 months.

11. The method of claim 1, wherein the quantity of neurotoxin administered is about 1 unit to about 50,000 units.

12. A method of controlling dysregulation of the Dorsal Cutaneous Nerve of the Clitoris in a human, comprising: administering a composition containing a neurotoxin to the clitoral area of the human; wherein the neurotoxin is a native botulinum toxin.

13. The method of claim 12, wherein the botulinum toxin is selected from the group consisting of botulinum toxin types A, B, C, D, E, F, and G.

14. The method of claim 13, wherein the botulinum toxin is type A or type B.

15. The method of claim 13, wherein the botulinum toxin is administered to the vulva.

16. The method of claim 13, wherein the botulinum toxin is administered to the periclitoral area.

17. The method of claim 13, wherein the botulinum is administered via instillation, orally, topically, via injection, via implant, or a combination thereof.

18. The method of claim 12, wherein the quantity of neurotoxin administered is about 1 unit to about 50,000 units.

* * * * *